(12) United States Patent
Little

(10) Patent No.: US 10,219,906 B2
(45) Date of Patent: Mar. 5, 2019

(54) GIRTH EXPANDING PENILE PROSTHESIS CYLINDER

(71) Applicant: Boston Scientific Scimed, Inc., Maple Grove, MN (US)

(72) Inventor: Eric F. Little, Skakopee, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 190 days.

(21) Appl. No.: 14/880,770

(22) Filed: Oct. 12, 2015

(65) Prior Publication Data

US 2016/0100945 A1     Apr. 14, 2016

Related U.S. Application Data

(60) Provisional application No. 62/063,106, filed on Oct. 13, 2014.

(51) Int. Cl.
*A61F 2/26* (2006.01)

(52) U.S. Cl.
CPC .......... *A61F 2/26* (2013.01); *A61F 2250/001* (2013.01); *A61F 2250/0003* (2013.01); *A61F 2250/0018* (2013.01); *A61F 2250/0036* (2013.01)

(58) Field of Classification Search
CPC ........ A61H 19/34; A61H 19/40; A61H 19/44; A61H 19/00; A61H 19/30; A61H 19/32
USPC ....................................................... 600/38–41
See application file for complete search history.

(56) References Cited

U.S. PATENT DOCUMENTS

| 4,235,227 | A | | 11/1980 | Yamanaka et al. |
| 4,523,584 | A | | 6/1985 | Yachia et al. |
| 4,532,920 | A | * | 8/1985 | Finney ...................... A61F 2/26 600/40 |
| 4,665,903 | A | * | 5/1987 | Whitehead ................ A61F 2/26 600/40 |
| 8,147,400 | B1 | * | 4/2012 | Daniel ...................... A61F 2/26 600/40 |
| 8,795,154 | B1 | * | 8/2014 | Hakky ...................... A61F 2/26 600/40 |
| 2009/0105530 | A1 | | 4/2009 | Kuyava et al. |
| 2009/0253953 | A1 | | 10/2009 | Morningstar et al. |

FOREIGN PATENT DOCUMENTS

WO     2016060989 A1    4/2016

OTHER PUBLICATIONS

International Preliminary Report on Patentability for PCT/US2015/055125, dated Apr. 27, 2017, 7 pages.
International Search Report and Written Opinion for PCT Application No. PCT/US2015/055125, dated Dec. 23, 2015, 11 pages.

* cited by examiner

*Primary Examiner* — Samuel Gilbert
(74) *Attorney, Agent, or Firm* — Brake Hughes Bellermann LLP

(57) ABSTRACT

An implantable inflatable penile prosthesis cylinder has a longitudinal axis and includes an inflatable portion. The inflatable portion includes a chamber that defines an inflatable chamber. The chamber wall includes at least one thin wall section and at least one thick wall section. The at least one thin wall section stretches a greater amount than the at least one thick wall section in a plane extending perpendicular to the longitudinal axis when the inflatable chamber is transitioned from a deflated state to an inflated state.

16 Claims, 4 Drawing Sheets

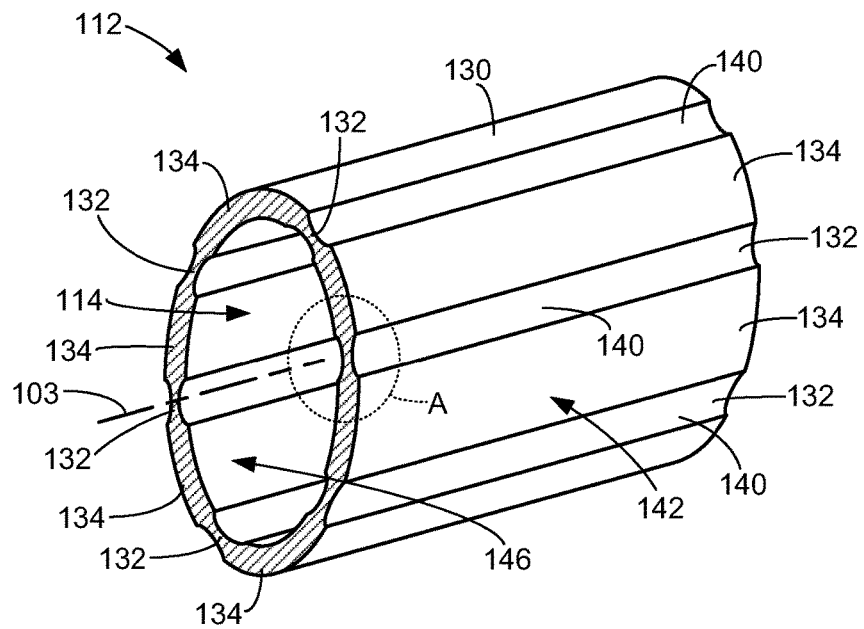
FIG. 2
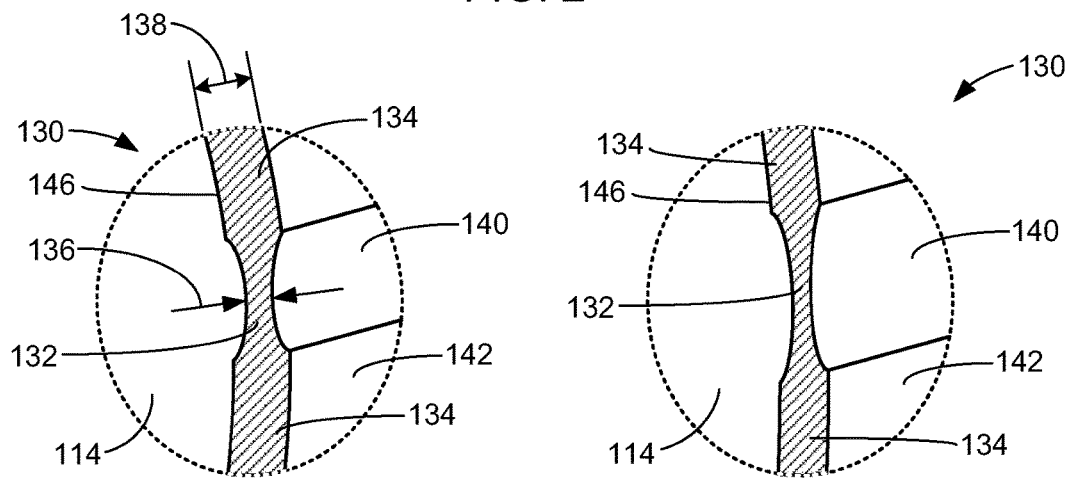
FIG. 3
FIG. 4

GIRTH EXPANDING PENILE PROSTHESIS CYLINDER

CROSS-REFERENCE TO RELATED APPLICATION

The present application is based on and claims the benefit of U.S. provisional patent application Ser. No. 62/063,106, filed Oct. 13, 2014, the content of which is hereby incorporated by reference in its entirety.

FIELD OF THE INVENTION

The invention generally relates to penile prostheses and, more specifically, to inflatable penile prosthesis cylinders having an expandable girth.

BACKGROUND OF THE INVENTION

Erectile dysfunction (ED) or impotence is the inability to get or keep an erection that is firm enough, or lasts long enough, to have successful sexual intercourse. It can have serious effects on a person's sexual relationship and their self-esteem.

Inflatable penile prostheses may be used to cure or compensate for impotence. Inflatable penile prostheses typically include a pair of inflatable cylinders and a pump. The cylinders are implanted in the corpus cavernosa of the patient, and the pump is implanted in the scrotum of the patient. For some inflatable penile prostheses (i.e., three-piece penile prostheses), a separate fluid reservoir must be implanted in the abdomen of the patient. Alternatively, the fluid reservoir may be combined with the cylinders (i.e., two-piece penile prostheses). Both the three-piece and the two-piece penile inflatable prostheses rely on the transfer of a volume of fluid from the reservoir to the cylinders, to transition the cylinders between deflated and inflated states, which respectively correspond to flaccid and erect penis conditions.

Conventional inflatable penile prosthesis cylinders generally have a uniform wall thickness. The cylinders may expand radially relative to a longitudinal axis of the cylinders when they are inflated. Such girth expansion capability is directly related to the cylinder pressure that can be generated by the patient to overcome the resistance of stretching the wall of the cylinder, or the "stack-up" pressure. The less pressure-generating capability a patient has, the smaller the girth expansion that is possible for each of the cylinders.

SUMMARY

Embodiments of the invention are generally directed to an implantable inflatable penile prosthesis cylinder having an expandable girth, and a penile prosthesis that includes the inflatable penile prosthesis cylinder. In some embodiments, the implantable inflatable penile prosthesis cylinder has a longitudinal axis and includes an inflatable portion. The inflatable portion includes a chamber that defines an inflatable chamber. The chamber wall includes at least one thin wall section and at least one thick wall section. The at least one thin wall section stretches a greater amount than the at least one thick wall section in a plane extending perpendicular to the longitudinal axis when the inflatable chamber is transitioned from a deflated state to an inflated state.

Some embodiments of the implantable penile prosthesis include a pair of inflatable penile prosthesis cylinders, a reservoir containing fluid, and an inflation apparatus. Each penile prosthesis cylinder has a longitudinal axis and includes an inflatable portion. The inflatable portion includes a chamber wall that defines an inflatable chamber. The chamber wall includes at least one thin wall section and at least one thick wall section. The inflation apparatus is configured to transfer fluid from the reservoir into the inflatable chamber to transition the inflatable portion to an inflated state. The at least one thin wall section stretches a greater amount than the at least one thick wall section in a plane extending perpendicular to the longitudinal axis when the inflatable chamber is transitioned from a deflated state to the inflated state.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the Background.

BRIEF DESCRIPTION OF THE DRAWINGS

FIG. 2 is a simplified partial cross-sectional isometric view of a section of an inflatable portion of the penile prosthesis cylinder of FIG. 1, in accordance with embodiments of the invention.

FIGS. 3 and 4 are magnified views of the portion A of FIG. 2 when the inflatable portion is in deflated and inflated states, respectively, in accordance with embodiments of the invention.

DETAILED DESCRIPTION OF ILLUSTRATIVE EMBODIMENTS

Figure 1:
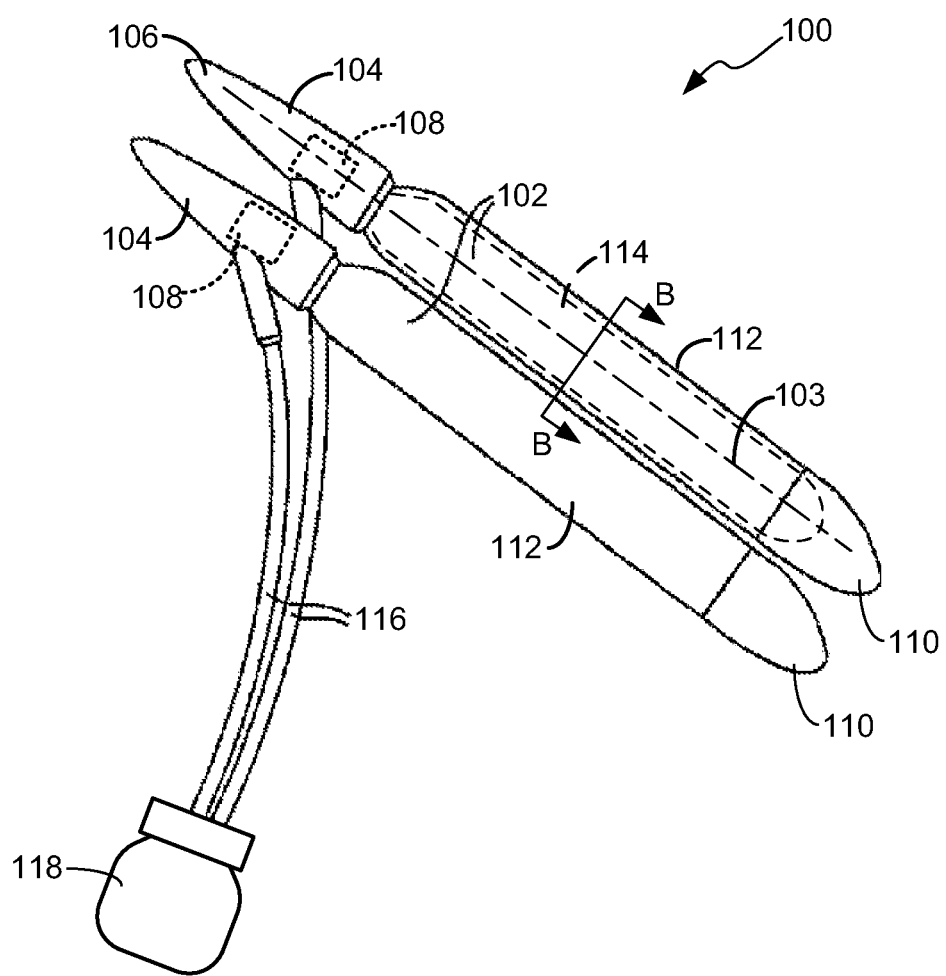
FIG. 1 is a schematic isometric view of an exemplary penile prosthesis comprising cylinders in accordance with one or more embodiments of the invention.
Figure 5:
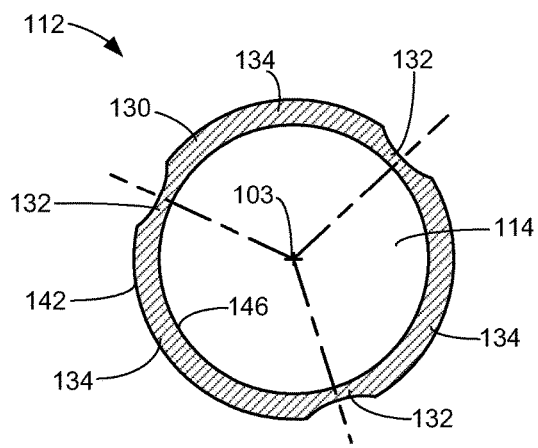
FIGS. 5-10 are cross-sectional views of an inflatable portion of a penile prosthesis cylinder of FIG. 1 taken generally along line B-B, in accordance with embodiments of the invention.
Figure 6:
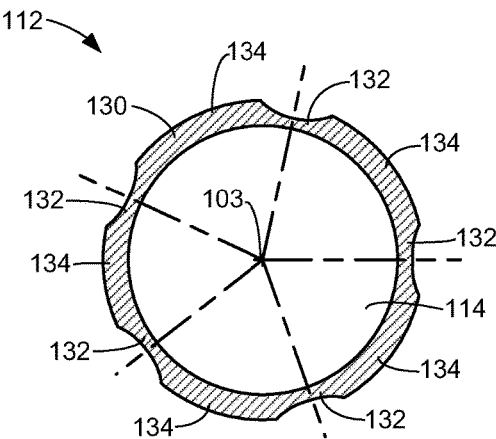

Embodiments of the invention are described more fully hereinafter with reference to the accompanying drawings. Elements that are identified using the same or similar reference characters refer to the same or similar elements. The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art.

Specific details are given in the following description to provide a thorough understanding of the embodiments. However, it is understood by those of ordinary skill in the art that the embodiments may be practiced without these specific details. For example, circuits, systems, networks, processes, frames, supports, connectors, motors, processors, and other components may not be shown, or shown in block diagram form in order to not obscure the embodiments in unnecessary detail.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1 is a schematic isometric view of an exemplary penile prosthesis 100 comprising cylinders 102 formed in accordance with one or more embodiments described herein. While the exemplary penile prosthesis 100 is depicted as a two-piece inflatable penile prosthesis, embodiments of the cylinders 102 may also be used with three-piece inflatable penile prostheses or other penile prostheses that utilize inflatable cylinders, as is readily apparent to those skilled in the relevant art.

Each of the penile prosthesis cylinders 102 is configured for implantation in a corpus cavernosum of a patient with a longitudinal axis 103 of the cylinder 102 generally aligned with a longitudinal axis of the corpus cavernosum. In some embodiments, the cylinders 102 include one or more conventional components, such as, for example a fluid reservoir 104 located in a rear portion 106, a fluid control block 108, and an end cap 110. In some embodiments, the fluid reservoir 104 and/or the fluid control block 108 may be located externally to the cylinders 102, such as in a three-piece penile prosthesis. The cylinders 102 may comprise other conventional components that are not shown in the drawings, such as an elastic (e.g., spandex) sleeve surrounding the exterior of the cylinders 102, for example.

In some embodiments, each of the cylinders 102 includes an inflatable portion 112 formed in accordance with one or more embodiments described herein. In some embodiments, the portion 112 includes a chamber 114 having a deflated state, in which the chamber 114 contains a relatively low volume of fluid, and an inflated state, in which the chamber 114 contains a relatively high volume of fluid. When the inflatable portion 112 or the chamber 114 is in the deflated condition, the corresponding cylinder 102 is relatively flexible and simulates a flaccid penis condition. When the inflatable portion 112 or the chamber 114 is in the inflated condition, the corresponding cylinder 102 is relatively stiff and simulates an erect penis condition.

In some embodiments, the penile prosthesis 100 includes tubing 116 that connects the fluid control block 108 to an inflation apparatus 118, such as a pump bulb or other suitable inflation apparatus, which is configured to drive fluid from the reservoir 104 and into the chamber 114 to transition the inflatable portion 112 and the chamber 114 from the deflated state to the inflated state. In some embodiments, the fluid control block 108 includes fluid pathways and valves for controlling the flow of fluid to and from the chamber 114 from the reservoir 104. In some embodiments, the inflation apparatus 118 is manually actuated by the user. In some embodiments, the inflation apparatus is driven by an electrical motor or other suitable device. Fluid contained in the chamber 114 of the inflatable portion 112 may be returned to the reservoir 104 of the cylinder 102 using conventional techniques to transition the inflatable portion 112 and the cylinder 102 back to the deflated state, such as by bending the cylinder 102, for example.

It is desirable for inflatable penile prosthesis cylinders to expand radially relative to their longitudinal axis to provide girth expansion for the patient. As mentioned above, the wall of the inflatable chamber in conventional inflatable penile prosthesis cylinders generally has a uniform thickness. The radial or girth expansion of such conventional penile prosthesis cylinders is directly related to the pressure that can be generated within the chamber by the patient to overcome the resistance of stretching the wall of the chamber, or the "stack-up" pressure. Unfortunately, many patients lack the ability to generate sufficient pressure to take full advantage of the girth expansion capability of conventional inflatable penile prosthesis cylinders. Embodiments of the cylinders 102 facilitate girth expansion while minimizing the stack-up pressure a user must overcome to fully inflate and radially expand the cylinders 102 relative to the longitudinal axis 103 (girth expansion).

Embodiments of the inflatable penile prosthesis cylinders 102 will be described with reference to FIGS. 2-10. FIG. 2 is a simplified partial cross-sectional isometric view of a section of an inflatable portion 112 of the penile prosthesis cylinder 102 of FIG. 1, in accordance with embodiments of the invention. FIGS. 3 and 4 are magnified views of the portion A of FIG. 2 when the inflatable portion 112 is in deflated and inflated states, respectively, in accordance with embodiments of the invention. FIGS. 5-10 are cross-sectional views of an inflatable portion 112 of the penile prosthesis cylinder 102 of FIG. 1 taken generally along line B-B, in accordance with embodiments of the invention.

In some embodiments, each of the penile prosthesis cylinders 102 includes a chamber wall 130 that defines the inflatable chamber 114 of the inflatable portion 112. In some embodiments, the wall 130 includes at least one thin wall section 132, and at least one thick wall section 134. Each thin wall section 130 has a thickness 136 that is less than the thickness 138 of the thick wall section 132, as shown in FIG. 3. In some embodiments, the thickness 138 of the thick wall sections 134 is generally in accordance with conventional inflatable chamber walls, while the thickness 136 of the thin wall sections 132 is generally less than that of conventional inflatable chamber walls. In some embodiments, the thick wall portions 134 have a thickness 138 in the range of 0.020-0.040 inch, and the thin wall sections 132 have a thickness 136 of less than 0.020 inch.

In some embodiments, the at least one thin wall section 132, includes two or more thin wall sections 132, three or more thin wall sections 132, four or more thin wall sections 132, five or more thin wall sections 132, and/or other desired number of thin wall sections 132. Accordingly, while the embodiments of the wall 130 shown in FIGS. 2 and 5-8 include up to eight thin wall sections 132 and thick wall sections 134, it is understood that the wall 130 may include more or fewer thin wall sections 132 and thick wall sections 134.

In some embodiments, the thin wall sections 132 are elongated along the longitudinal axis 103, as shown in FIG. 2. In some embodiments, the at least one thin wall section 132 and the at least one thick wall section 130 are angularly displaced from each other around the longitudinal axis, as shown in FIGS. 2 and 5-8. In some embodiments, each of the at least one thin wall sections 132 are positioned between pairs of thick wall sections 134, and/or each of the at least one thick wall section 134 is positioned between pairs of thin wall sections 132, in a plane extending perpendicular to the longitudinal axis 103, as in the cross-sectional portion of FIG. 2.

In some embodiments, the thin wall sections 132 are formed by recesses 140 formed in an outside surface 142 of the chamber wall 130, and/or an inside surface 146 of the chamber wall 130, as shown in FIG. 2. In some embodiments, the recesses 140 provide a smooth transition in the thickness of the wall 130 from an adjoining thick wall section 134 to the thin wall section 132.

For a given pressure within the inflatable chamber 114, the stress within the thin wall sections 132 is greater than the stress within the thick wall sections 134 due to the smaller cross-sectional area of the thin wall sections 132. In some embodiments, the material forming the thin wall sections 132 and the thick wall sections 134 is the same. In some embodiments, the wall 130 is formed of silicone or other suitable material. As a result, the material forming the chamber wall 130 will stretch more in the thin wall sections 132 than in the thick wall sections 134 responsive to a given pressure in the inflatable chamber 114. Thus, the thin wall sections 132 stretch a greater distance than the thick wall sections 134 in a plane extending perpendicularly to the longitudinal axis 103, when the inflatable portion 112 and the chamber 114 transition from a deflated state (FIG. 3) to an inflated state (FIG. 4).

For a given pressure within the inflatable chamber 114, the circumference of the chamber wall 130 and the girth of the cylinder 102 expand a greater amount than would be possible if the cylinder 102 had a uniform thickness corresponding to the thick wall sections 134. This is due to the thin wall sections 132 lowering the "stack-up" pressure, which reduces the effort required by the user to inflate the cylinder 102 using the inflation apparatus 118. Additionally, the thin wall sections 132 also allow for the girth of the cylinder 102 to expand more than conventional penile prosthesis cylinders 102. In some embodiments, each cylinder 102 includes an outer elastic or spandex sleeve to constrain this radial expansion of the inflatable portion 112.

Figure 7:
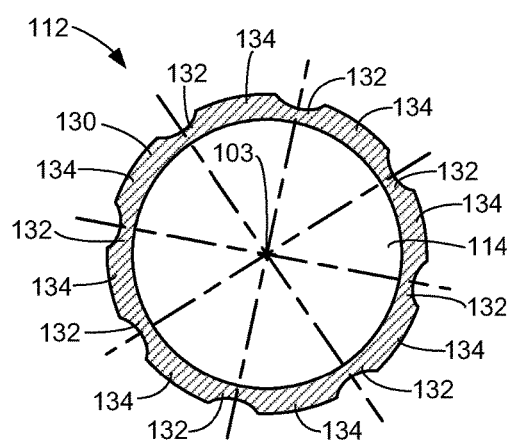
Figure 8:
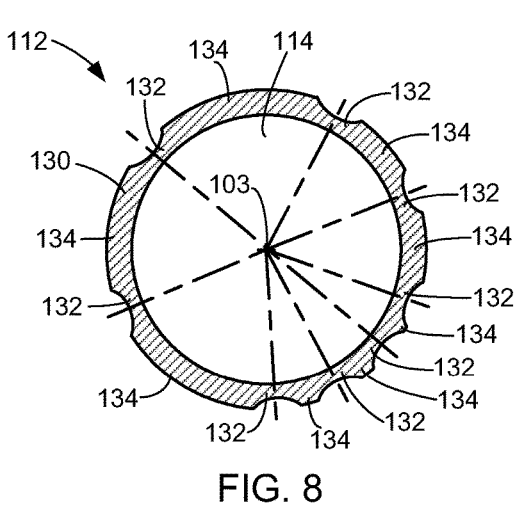

In some embodiments, the thin wall sections 132 are uniformly angularly distributed around the periphery of the inflatable portion 112 or the cylinder 102 about the axis 103, as generally shown in FIGS. 2 and 5-7. In some embodiments, the thin wall sections 132 are non-uniformly displaced around the periphery of the cylinder 102 about the axis 114, as shown in FIG. 8. As a result, the location of expansion of the wall 130 of the inflatable portion 112 may be customized to provide a location for greater wall stress, which can be used to form a bulge in the wall 130 having a larger radial expansion relative to the longitudinal axis 103 than other areas.

Figure 9:
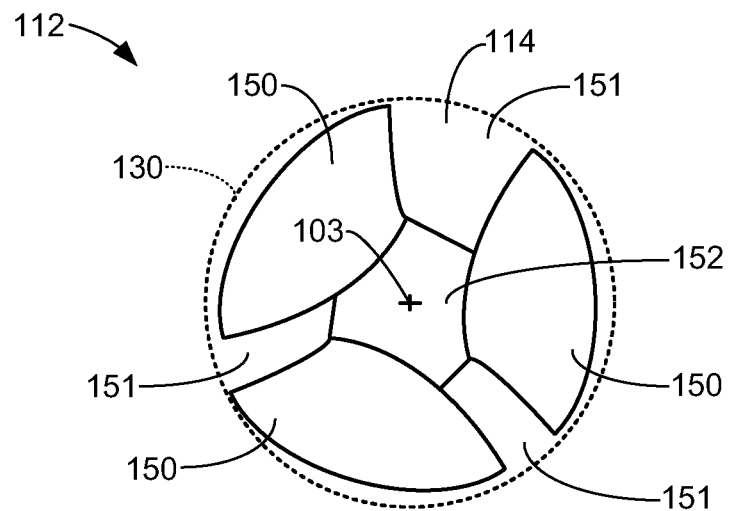
Figure 10:
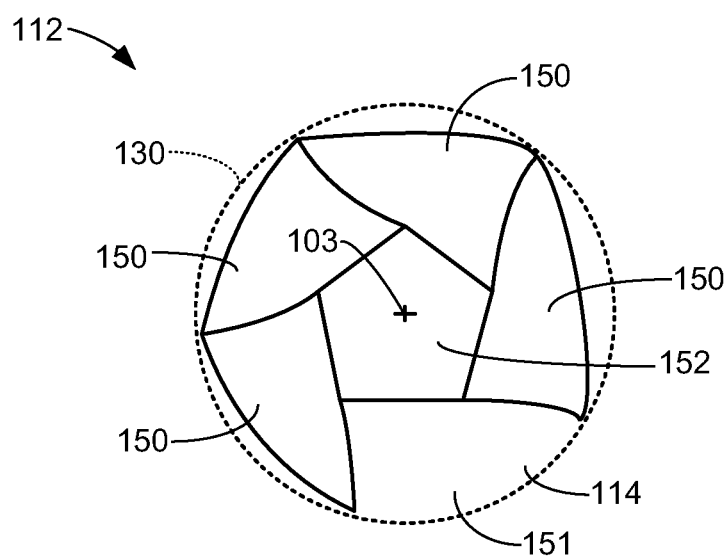

In some embodiments, each cylinder 102 includes two or more inflatable sub-chambers 150, within the chamber wall 130 (indicated in phantom lines) defining the chamber 114 of the inflatable portion 112, as shown in FIGS. 9 and 10. In some embodiments, the inflatable sub-chambers 150 extend along the longitudinal axis 103 of the cylinder 102 within the inflatable portion 112.

In some embodiments, the sub-chambers 150 are configured to receive fluid driven by the inflation apparatus 118 to transition the sub-chambers 150 and the inflatable chamber 114 from a deflated condition to an inflated condition. In some embodiments, only the sub-chambers 150 receive fluid from the reservoir 104 during an inflation operation. As a result, the sub-chambers 150 facilitate a reduction in the amount of fluid that must be driven into the inflatable chamber 114 to transition the chamber 114 to the inflated state due to gaps 151 within the inflatable chamber 114, for example.

In some embodiments, one or more gaps 151 are formed between at least two adjacent sub-chambers 150. For instance, the gaps 151 may exist between each pair of adjacent sub-chambers 150, as shown in FIG. 9, or the gaps 151 may be located only between a single pair of adjacent sub-chambers 150, as shown in FIG. 7, for example.

In some embodiments, the penile prosthesis cylinder 102 includes a central member 152, which may be attached to the sub-chambers 150. In some embodiments, the inflatable sub-chambers 150 are outer chambers that extend radially from the central member 152, as shown in FIGS. 9 and 10. In some embodiments, the central member 152 comprises a structure that supports the sub-chambers 150 during inflation. Thus, in this embodiment, the central member 152 operates as one of the gaps 151. In some embodiments, the central member 152 is also an inflatable sub-chamber 150 that is inflated with fluid driven from the inflation apparatus 118.

The foregoing examples have focused on embodiments of an implantable inflatable penile prosthesis cylinder 102 for use in a penile prosthesis 100 to treat erectile dysfunction. The cylinder 102 includes an inflatable portion 112 that is configured to be transitioned from a deflated state to an inflated state through the reception of fluid within an inflatable chamber 114. The girth of at least the inflatable portion 112, measured in a plane extending perpendicularly to a longitudinal axis 103 of the cylinder 102, expands through the stretching of thin wall sections 132 of a chamber wall 130 in response to the inflation of the chamber 114. Other embodiments have focused on an implantable penile prosthesis 100 that includes a pair of the inflatable penile prosthesis cylinders 102 formed in accordance with one or more embodiments described herein. In some embodiments, the expansion of the girth of the cylinders 102 is achieved with less user effort because the pressure required to perform the expansion is reduced due to the at least one thin wall section 132. Additionally, in some embodiments, the amount of fluid required to be transferred into the inflatable chamber 114 is reduced due to the use of sub-chambers 150.

Although the present invention has been described with reference to preferred embodiments, workers skilled in the art will recognize that changes may be made in form and detail without departing from the spirit and scope of the invention.

What is claimed is:

1. An implantable inflatable penile prosthesis cylinder having a longitudinal axis, comprising:
    an inflatable portion including a chamber wall defining an inflatable chamber, the chamber wall including a plurality of thin wall sections and a plurality of thick wall sections, the plurality of thin wall sections having at least one edge and the plurality of thick wall sections at least one edge, the edges of the plurality of thin wall sections being joined to the edges of the plurality of thick wall sections to form the chamber wall in a continuous radial manner, each of the plurality of thin wall sections being disposed between a pair of the thick wall sections, the plurality of thin wall sections being angularly displaced from each other about the longitudinal axis, wherein the plurality of thin wall sections stretch a greater amount than the plurality of thick wall sections in a plane extending perpendicular to the longitudinal axis when the inflatable chamber is transitioned from a deflated state to an inflated state.

2. The inflatable penile prosthesis cylinder according to claim 1, wherein the thin wall sections are uniformly angularly distributed from each other about the longitudinal axis.

3. The inflatable penile prosthesis cylinder according to claim 1, wherein the thin wall sections are non-uniformly angularly distributed from each other about the longitudinal axis.

4. The inflatable penile prosthesis cylinder according to claim 1, wherein at least one of the plurality of thin wall sections has a thickness of less than 0.020 inches, and at least one of the plurality of thick wall sections has a thickness of greater than 0.020 inches.

5. The inflatable penile prosthesis cylinder according to claim 1, wherein the thin wall sections extend along the longitudinal axis.

6. The inflatable penile prosthesis cylinder according to claim 1, wherein the thin wall sections and the thick wall sections are formed of a same material.

7. The inflatable penile prosthesis cylinder according to claim 1, wherein the thin wall sections and the thick wall sections are formed of silicone.

8. The inflatable penile prosthesis cylinder according to claim 1, further comprising a plurality of inflatable chamber sections within the inflatable chamber, wherein inflation of the plurality of inflatable chamber sections transitions the inflatable chamber to the inflated state.

9. The inflatable penile prosthesis cylinder according to claim 1, further comprising a fluid reservoir and fluid pathways connecting the fluid reservoir to the inflatable chamber.

10. An implantable penile prosthesis comprising:
a pair of inflatable penile prosthesis cylinders, each of the penile prosthesis cylinders having a longitudinal axis and including an inflatable portion including a chamber wall defining an inflatable chamber, the chamber wall including a plurality of thin wall sections and a plurality of thick wall sections, the plurality of thin wall sections being formed by a recess disposed on a surface of the chamber wall, the recess configured to provide a transition to an adjoining thick wall section, each of the plurality of thin wall sections being disposed between a pair of the thick wall sections, the plurality of thin wall sections being angularly displaced from each other about the longitudinal axis;
a reservoir containing fluid; and
an inflation apparatus configured to transfer the fluid from the reservoir into the inflatable chamber to transition the inflatable portion to an inflated state,
wherein the plurality of thin wall sections stretch a greater amount than the plurality of thick wall sections in a plane extending perpendicular to the longitudinal axis when the inflatable chamber is transitioned from a deflated state to the inflated state.

11. The implantable penile prosthesis according to claim 10, wherein the thin wall sections are uniformly angularly distributed from each other about the longitudinal axis.

12. The implantable penile prosthesis according to claim 10, wherein the thin wall sections are non-uniformly angularly distributed from each other about the longitudinal axis.

13. The implantable penile prosthesis according to claim 10, wherein at least one of the plurality of thin wall sections has a thickness of less than 0.020 inches, and at least one of the plurality of thick wall sections has a thickness of greater than 0.020 inches.

14. The implantable penile prosthesis according to claim 10, wherein the thin wall sections extend along the longitudinal axis.

15. The implantable penile prosthesis according to claim 10, further comprising a plurality of inflatable chamber sections within the inflatable chamber, wherein inflation of the plurality of inflatable chamber sections transitions the inflatable chamber to the inflated state.

16. An implantable inflatable penile prosthesis cylinder having a longitudinal axis, comprising:
an inflatable portion including a chamber wall defining an inflatable chamber, the chamber wall including a plurality of thin wall sections and a plurality of thick wall sections, the plurality of thin wall sections having at least one edge and the plurality of thick wall sections at least one edge, each of the plurality of thin wall sections being disposed between a pair of the thick wall sections, the plurality of thin wall sections being angularly displaced from each other about the longitudinal axis, wherein both of the plurality of thin wall sections and the plurality of thick wall sections stretch in a plane extending perpendicular to the longitudinal axis when the inflatable chamber is transitioned from a deflated state to an inflated state, the plurality of thin wall sections stretching a greater amount than the plurality of thick wall sections.

* * * * *